United States Patent [19]

Crochemore

[11] Patent Number: 4,933,498

[45] Date of Patent: Jun. 12, 1990

[54] PREPARATION OF TRIALKOXYBENZALDEHYDES

[75] Inventor: Michel Crochemore, Chaponost, France

[73] Assignee: Rhone-Poulenc Chimie, Courbevoie, France

[21] Appl. No.: 391,410

[22] Filed: Aug. 7, 1989

Related U.S. Application Data

[63] Continuation of Ser. No. 149,660, Jan. 28, 1988, abandoned.

[30] Foreign Application Priority Data

Jan. 28, 1987 [FR] France .................................. 8701174

[51] Int. Cl.$^5$ ............................................. C07C 47/548
[52] U.S. Cl. ..................................................... 568/433
[58] Field of Search ........................................... 568/933

[56] References Cited

FOREIGN PATENT DOCUMENTS 0100451 2/1984 European Pat. Off. ............ 568/433

OTHER PUBLICATIONS

Pearl et al., *J. Am. Chem. Soc.*, vol. 74, pp. 4262–4263 (1952).

*Primary Examiner*—Bruce Gray
*Attorney, Agent, or Firm*—Burns, Doane, Swecker & Mathis

[57] ABSTRACT

3,4,5-Trialkoxybenzaldehydes, notably 3,4,5-triamethoxybenzaldehyde, are prepared by hydrolyzing 5-bromo-4-hydroxy-3-methoxybenzaldehyde with an alkali metal hydroxide, in water and in the presence of a copper catalyst, and then directly sequentially (i.e., without separating any reaction intermediates) etherifying the 4,5-dihydroxy-3-methoxybenzaldehyde thus produced with a lower alkyl halide, in an aqueous medium and at a pH maintained at a value of from 6 to 12, optionally in the presence of a catalyst.

17 Claims, No Drawings

PREPARATION OF TRIALKOXYBENZALDEHYDES

This application is a continuation of application Ser. No. 07/149,660, filed Jan. 28, 1988 now abandoned.

BACKGROUND OF THE INVENTION

1. Field of the Invention

The present invention relates to an improved process for the preparation of 3,4,5-trialkoxybenzaldehyde, and, more especially, for the preparation of 3,4,5-trimethoxybenzaldehyde from a 5-bromo-4-hydroxy-3-methoxybenzaldehyde starting material.

2. Description of the Prior Art

The most common technique in this art for the production of 3,4,5-trimethoxybenzaldehyde starting with 5-bromo-4-hydroxy-3-methoxybenzaldehyde (or 5-bromovanillin) consists in hydrolyzing the bromine atom using an aqueous sodium hydroxide solution, in the presence of copper.

After isolating the 4,5-dihydroxy-3-methoxybenzaldehyde (or 5-hydroxyvanillin) produced, the latter is methylated using dimethyl sulfate or methyl chloride.

Thus, published French Patent application No. 2,177,693 describes the methylation of 5-hydroxyvanillin by dimethyl sulfate in the presence of an alkali metal carbonate.

5-Hydroxyvanillin is itself produced by hydrolyzing 5-bromovanillin and is then extracted, especially with toluene for 47 hours, recrystallized, washed and dried.

The stage of isolating the 5-hydroxyvanillin is therefore quite lengthy and expensive. Additionally, the catalyst cannot be recovered and recycled.

SUMMARY OF THE INVENTION

Accordingly, a major object of the present invention is the provision of an improved process for the hydrolysis of 5-bromovanillin and subsequent etherification of the 5-hydroxyvanillin thus produced, in sequence, without the necessity for an intermediate separation of the 5-hydroxyvanillin.

An added advantage of the process of the invention is that the copper used as catalyst for the hydrolysis of 5-bromovanillin may be recovered and recycled into a subsequent operation.

Briefly, the present invention features the preparation of 4,5-dialkoxy-3-methoxybenzaldehyde, without the necessity of separating any reaction intermediate compounds, by (a) hydrolyzing 5-bromo-4-hydroxy-3-methoxybenzaldehyde into 4,5-dihydroxy-3-methoxybenzaldehyde utilizing an alkali metal hydroxide, in water and in the presence of a copper catalyst; and (b) sequentially etherifying the 4,5-dihydroxy-3-methoxybenzaldehyde thus produced with a lower alkyl halide, in an aqueous medium and maintaining the pH of the reaction medium at a value of from 6 to 12, optionally in the presence of a catalyst.

DETAILED DESCRIPTION OF THE PREFERRED EMBODIMENTS OF THE INVENTION

More particularly according to the present invention, it has been determined that, when the reaction is carried out at a pH below 6, a significant hydrolysis of the alkyl halide and a quantitative decrease in the etherification result, as well as a decrease in the speed of this reaction.

All alkali metal hydroxides may be employed in the first reaction of the subject process. However, for reasons of cost, sodium hydroxide is preferred.

At least one mole of alkali metal hydroxide per mole of 5-bromo-4-hydroxy-3-methoxybenzaldehyde is usually employed. However, an excess of alkali metal hydroxide is preferably employed. Most preferably, the molar ratio alkali metal hydroxide:5-bromo-4-hydroxy-3-methoxybenzaldehyde ranges from 2 to 5.

The amount of water in the reaction medium is not critical. However, considering the low solubility of 5-bromo-4-hydroxy-3-methoxybenzaldehyde, the weight of this compound relative to the weight of water generally ranges from 5 to 20%.

The copper catalyst may be copper metal or any one of its organic or inorganic derivatives. Representative are, for example, a copper oxide, a copper hydroxide, a copper sulfate, a copper nitrate, a copper chloride, a copper acetate, a copper phenate, or any other copper compound.

Copper metal is often employed because it is easy to use; in the reaction medium, this copper metal is at least partially converted into hydroxide or into the copper derivative of the different reagents present.

A molar ratio copper compound:5-bromo-4-hydroxy-3-methoxybenzaldehyde from 1 to 10% is generally employed. This molar ratio preferably ranges from 3 to 7%.

The temperature at which the reaction is carried out generally ranges from 50° to 250° and preferably from 100° to 200° C.

The 5-bromo-4-hydroxy-3-methoxybenzaldehyde starting material may be prepared in a manner known per se. The bromination of vanillin may especially be carried out with bromine in an acid solution. Compare, in this respect, the process described in published French Patent Application No. 2,177,693.

The vanillin may also be brominated using a hydrobromic acid+hydrogen peroxide system as described in published French Patent Application No. 2,557,097, or using a bromine+hydrogen peroxide system as described in published French Patent Application No. 2,557,098.

The second reaction of the process of the invention is carried out using the aqueous solution obtained during the first reaction, comprising the 4,5-dihydroxy-3-methoxybenzaldehyde, and a lower alkyl halide.

By "lower alkyl" is intended a straight or branched chain alkyl group containing 1 to 4 carbon atoms.

A methyl halide or an ethyl halide is most advantageously employed.

Among the halides, the chlorides, bromides and iodides are generally employed and, more specifically, methyl chloride, chloroethane, methyl bromide and bromoethane.

Because of their lower cost, the use of methyl chloride and chloroethane is preferred.

Among the 4,5-dialkoxy-3-methoxybenzaldehydes which are prepared by the process of the invention, 3,4,5-trimethoxybenzaldehyde (TMBA) is the one which has the largest number of known uses, especially as an intermediate for the preparation of pharmaceutical products.

An excess of alkyl halide relative to stoichiometry is generally employed.

In one preferred embodiment of the invention, the etherification reaction is carried out in a two-phase medium consisting of water and a water-immiscible organic solvent.

The water-immiscible solvents capable of being employed in the etherification reaction may be very diverse in nature.

It is possible to employ, for example, an aromatic hydrocarbon such as benzene, toluene or xylenes. It is also possible to employ an aliphatic or alicyclic hydrocarbon such as hexane, heptane, octane, decane or cyclohexane; chlorinated aromatic hydrocarbons are also suitable. Thus, it is possible to employ the different chlorobenzenes (for example monochlorobenzene and dichlorobenzenes), or aliphatic, aromatic or arylaliphatic ethers such as, for example, dibutyl ether, dipentyl ether, dipropyl ether, diisopropyl ether, ethyl pentyl ether, anisole or dibenzyl ether.

An aromatic hydrocarbon or an ether is generally employed.

The temperature for the etherification reaction is not critical, although it does affect the reaction rate. The etherification is generally carried out at a temperature of from 50° C. to 150° C. The reaction is preferably carried out at a temperature of from 90° C. to 120° C.

The pressure is not critical. It also has an effect on the reaction rate. It usually varies from atmospheric pressure to 50 bars.

The choice of a higher or a lower pressure will depend especially on the presence or the absence of catalyst. In the presence of catalyst, the greater the amount of catalyst, the lower will be the pressure, i.e., it may, for example, range from atmospheric pressure to 20 bars.

The pressure is usually created by the alkyl halide used for the etherification, when it is gaseous under the reaction conditions.

The presence of catalyst is not indispensable. However, it is generally advantageous to catalyze the reaction such as to achieve a higher reaction rate and milder conditions, especially of pressure.

The catalyst is advantageously selected from among the amines and quaternary ammonium salts.

All primary, secondary or tertiary amines may be used.

Thus, it is possible to use aliphatic, aromatic, arylaliphatic, alicyclic or heterocyclic primary and secondary amines.

Exemplary of such amines, representative are ethylamine, propylamine, butylamine, hexylamine, octylamine, decylamine, laurylamine, dimethylamine, dipropylamine, diisopropylamine, dibutylamine, diisobutylamine, dihexylamine, aniline, piperidine, benzylamine, methylaniline, ethylaniline, pyrrolidine and imidazole.

The tertiary amines which may be used are also very diverse. Representative are, for example, trialkylamines, the alkyl radicals of which may be identical or different and may contain 1 to 24 carbon atoms; cycloalkylalkylamines; benzylalkylamines; phenylalkylamines or cyclic amines. These amines may bear other substituents such as ether or hydroxyl groups.

Exemplary are trimethylamine, triethylamine, tripropylamine, tributylamine, ethyldimethylamine, lauryldimethylamine, octadecyldimethylamine, propyldimethylamine, pentyldimethylamine, benzyldimethylamine, trioctylamine, triethanolamine, N,N-dimethylaniline, butyldimethylamine, N,N-diethylaniline, N-methylpiperidine, N-ethylpiperidine, N-methylpyrrolidine, N-methylimidazole, pyridine, 3-methylpyridine, 2-methylpyridine, 4-methylpyridine, 2,4-dimethylpyridine, 2,6-dimethylpyridine and triethylenediamine.

It is, of course, possible to employ industrial mixtures (industrial cuts) of different amines, which are commercially available.

The use of amines which can be most easily quaternized under the reaction conditions is generally preferred.

It is also possible to use quaternary ammonium salts as catalyst. These are, for example, alkyl, cycloalkyl or benzyl halides, hydroxides or sulfates derived from the above amines.

Quaternary ammonium chlorides or bromides are generally preferred.

The amount of catalyst employed may vary over very wide limits.

0 to 30 mole % of catalyst relative to the 4,5-dihydroxy-3-methoxybenzaldehyde and to the other hydroxybenzaldehydes possibly present are generally employed.

This molar ratio preferably ranges from 0 to 20%.

The etherification catalyst may be introduced either as early as during the hydrolysis reaction, or only during the etherification reaction.

The pH of the reaction medium is maintained at the desired value of from 6 to 12 during the period of the etherification reaction.

This is done by injecting or introducing a solution of a base which is generally the alkali metal hydroxide employed in the reaction of hydrolysis of the 5-bromo-4-hydroxy-3-methoxybenzaldehyde.

The pH of the medium is preferably maintained at a value of from 9 to 11.

The copper catalyst which was employed during the hydrolysis reaction precipitates in the form of copper oxide, which can be filtered, recovered and reused in a new hydrolysis reaction.

One of the advantages of the process according to the invention is that it enables the catalyst for the hydrolysis reaction to be easily recovered or recycled, especially because of the virtually complete conversion rate during the etherification reaction.

In order to further illustrate the present invention and the advantages thereof, the following specific examples are given, it being understood that same are intended only as illustrative and in nowise limitative.

EXAMPLES 1a AND 1b

EXAMPLE 1a

The following materials were charged into a 1.5 liter stainless steel reactor equipped with a heating system and a stirrer:

(i) 99.2 g (0.428 mole) of 5-bromo-4-hydroxy-3-methoxybenzaldehyde (BHMB);

(ii) 68.8 g of sodium hydroxide pellets (1.72 mole);

(iii) 1.6 g of copper metal in the powdery form (0.025 mole) 800 cm$^3$ of water.

The mixture was heated, under stirring, for 2 hours at 150° C. in order to carry out the hydrolysis.

The mixture was then cooled to 100° C.; the pH of the reaction mixture was adjusted to 10 using sulfuric acid.

6.0 g (0.019 mole) of tributylbenzylammonium chloride and 150 cm$^3$ of toluene were introduced.

A pressure of 6 bars of methyl chloride was established and maintained constant throughout the period of the experiment.

The pH of the reaction mixture was maintained at 10 by injecting a 30% by weight aqueous sodium hydroxide solution.

After 2 hours of reaction at 100° C., the final reaction mixture was cooled and withdrawn.

The reactor was rinsed with 100 cm³ of water and then with 100 cm³ of toluene. These washings were combined with the reaction mixture.

The insoluble portion (cuprous oxide) was filtered, washed and dried; 1.8 g of Cu₂O were found (corresponding to the entire amount of copper employed).

The aqueous and the organic phases were separated.

The main constituents of the two phases were analyzed by high pressure liquid chromatography (HPLC):

| | |
|---|---|
| Conversion rate (CR) of BHMB | 100% |
| Yield (Y) of trimethoxybenzaldehyde (TMBA) relative to the BHMB converted | 80% |
| Y of 3,4-dimethoxybenzaldehyde relative to the BHMB converted | 14% |

During the hydrolysis of the BHMB, a small amount of vanillin was formed as by-product. During the etherification, this vanillin formed 3,4-dimethoxybenzaldehyde which was separated by distillation and valorized.

EXAMPLE 1b

The same quantities of the same reagents as in Example 1a were charged into the reactor described above, but the copper used as catalyst was replaced with the catalyst recovered in Example 1a (Cu₂O).

The operating conditions for the etherification were the same as in Example 1a, with the exception of temperature (110° C. instead of 100° C.) and time (1 hr, 45 min, instead of 2 hr).

The treatment of the final reaction mixture was the same as that described in 1a and the results obtained were as follows:

| | |
|---|---|
| CR of BHMB | 100% |
| Y of TMBA | 85% |
| Y of 3,4-dimethoxybenzaldehyde | 12% |
| Recovery of copper catalyst | 100% |

EXAMPLE 2

The following materials were charged into the apparatus described in Example 1:

(i) 99.2 g (0.428 mole) of 5-bromo-4-hydroxy-3-methoxybenzaldehyde (BHMB);
(ii) 66.8 g of sodium hydroxide pellets (1.67 mole);
(iii) 1.6 g of copper metal in the powdery form (0.025 mole);
(iv) 6 g of tributylbenzylammonium chloride (0.019 mole);
(v) 800 cm³ of water.

The hydrolysis reaction was carried out by heating, under stirring, for 4 hours at 135° C.

The etherification was carried out as described in Example 1a for 2 hours at 100° C., maintaining the pH of the reaction mixture at 10 during the period of the experiment, by injecting a 30% by weight aqueous sodium hydroxide solution and maintaining a methyl chloride pressure of 6 bars.

The treatment and the analyses of the final reaction mixture were the same as those described in Example 1a and the results obtained were as follows:

| | |
|---|---|
| CR of BHMB | 100% |
| Y of TMBA | 85% |
| Y of 3,4-dimethoxybenzaldehyde | 12% |
| Recovery of copper catalyst | 100% |

EXAMPLE 3

The etherification reaction was carried out without catalyst.

The following materials were charged into the apparatus described in Example 1:

(i) 99.2 g (0.428 mole) of 5-bromo-4-hydroxy-3-methoxybenzaldehyde (BHMB);
(ii) 66.8 g of sodium hydroxide pellets (1.67 mole);
(iii) 1.6 g of copper metal in the powdery form (0.025 mole);
(iv) 800 cm³ of water.

The hydrolysis reaction was carried out by heating, under stirring, for 4 hours at 135° C.

After cooling to 100° C. and adjusting the pH to 10 as in Example 1, 150 cm³ of toluene were charged and the etherification reaction was carried out for 4 hr, 30 min, at 100° C., at pH 10 (maintained by injecting a 30% by weight aqueous sodium hydroxide solution) and maintaining throughout the period of the experiment a methyl chloride pressure of 10 bars.

The treatment and the analyses of the final reaction mixture were the same as those described in Example 1a and the following results were obtained:

| | |
|---|---|
| CR of BHMB | 100% |
| Y of TMBA | 80% |
| Y of 3,4-dimethoxybenzaldehyde | 13.5% |
| Recovery | 100% |

EXAMPLE 4

Example 3 was repeated with the same charges, the same operating conditions and the same treatment, but without adding toluene before the etherification reaction was carried out.

The following results were obtained:

| | |
|---|---|
| CR of BHMB | 100% |
| Y of TMBA | 80% |
| Y of 3,4-dimethoxybenzaldehyde | 15% |
| Recovery of copper catalyst | 100% |

EXAMPLE 5

850 cm³ of an aqueous solution containing sodium hydroxide, originating from the hydrolysis of 5-bromo-4-hydroxy-3-methoxybenzaldehyde and containing the following materials, were charged into the apparatus described in Example 1:

(i) 0.333 mole of 4,5-dihydroxy-3-methoxybenzaldehyde (DHMB);
(ii) 0.074 mole of vanillin;
(iii) 0.022 mole of copper originating from the catalysis of the hydrolysis reaction.

150 cm³ of toluene and 23.9 g (0.074 mole) of tetrabutylammonium bromide were added.

The mixture was heated to 100° C., under stirring and the pH was adjusted to 10.

This pH value was maintained throughout the period of the experiment by injecting a 30% by weight aqueous sodium hydroxide solution.

A methyl chloride pressure of 3 bars was established and this value was maintained throughout the period of the experiment.

After 2 hr, 30 min, of reaction, the final reaction mixture was cooled and treated as described in Example 1a.

The following results were obtained:

| | |
|---|---|
| CR of DHMB | 100% |
| Y of TMBA | 97% |
| CR of vanillin | 100% |
| Y of 3,4-dimethoxybenzaldehyde | 92.5% |
| Recovery of copper catalyst | 100% |

EXAMPLE 6

860 cm³ of an aqueous solution containing sodium hydroxide, originating from the hydrolysis of 5-bromo-4-hydroxy-3-methoxybenzaldehyde and containing the following materials, were charged into the apparatus described in Example 1:

(i) 0.314 mole of 4,5-dihydroxy-3-methoxybenzaldehyde (DHMB);

(ii) 0.057 mole of vanillin;

(iii) 0.0205 mole of copper originating from the catalysis of the hydrolysis reaction.

140 cm³ of toluene and 12.7 g (0.069 mole) of tributylamine were added.

The mixture was heated to 105° C., under stirring and the pH was adjusted to 9.5. This pH value was maintained throughout the period of the experiment, by injecting a 30% by weight aqueous sodium hydroxide solution.

A methyl chloride pressure of 6 bars was established and this value was maintained throughout the period of the experiment.

After 2 hr, 30 min, of reaction, the final reaction mixture was cooled and treated as mentioned in Example 1a.

The following results were obtained:

| | |
|---|---|
| CR of DHMB | 100% |
| Y of TMBA | 99% |
| CR of vanillin | 100% |
| Y of 3,4-dimethoxybenzaldehyde | 100% |
| Recovery of copper catalyst | 100% |

EXAMPLE 7

Example 6 was repeated with the same charges and under the same operating conditions, with the exception of the methyl chloride pressure which was maintained at 10 bars instead of 6 bars. The reaction time was 1 hr, 40 min.

The following results were obtained:

| | |
|---|---|
| CR of DHMB | 100% |
| Y of TMBA | 95% |
| CR of vanillin | 100% |
| Y of 3,4-dimethoxybenzaldehyde | 100% |
| Recovery of copper catalyst | 100% |

EXAMPLE 8

950 g of an aqueous solution containing sodium hydroxide, originating from the hydrolysis of 5-bromo-4-hydroxy-3-methoxybenzaldehyde and containing the following materials, were charged into the apparatus described in Example 1:

(i) 0.314 mole of 4,5-dihydroxy-3-methoxybenzaldehyde (DHMB);

(ii) 0.057 mole of vanillin;

(iii) 0.205 mole of copper originating from the catalysis of the hydrolysis reaction.

140 cm³ of toluene and 10.6 g (0.034 mole) of tributylbenzylammonium chloride were added.

The mixture was heated to 100° C., under stirring and the pH was adjusted to 10.

This pH value was maintained throughout the period of the experiment by injecting a 30% by weight aqueous sodium hydroxide solution.

A methyl chloride pressure of 6 bars was established and this value was maintained throughout the period of the experiment.

After 1 hr, 15 min, of reaction, the final reaction mixture was cooled and treated as described in Example 1a.

The following results were obtained:

| | |
|---|---|
| CR of DHMB | 100% |
| Y of TMBA | 100% |
| CR of vanillin | 100% |
| Y of 3,4-dimethoxybenzaldehyde | 100% |
| Recovery of copper catalyst | 100% |

EXAMPLE 9

Example 8 was repeated with the same charges and under the same operating conditions, but the toluene was replaced with the same volume of diisopropyl ether.

The following results were obtained:

| | |
|---|---|
| CR of DHMB | 100% |
| Y of TMBA | 100% |
| CR of vanillin | 100% |
| Y of 3,4-dimethoxybenzaldehyde | 100% |
| Recovery of copper catalyst | 100% |

EXAMPLES 10 to 16

640 cm³ of an aqueous solution containing the following materials were charged into the apparatus described in Example 1:

(i) 0.893 mole of 4,5-dihydroxy-3-methoxybenzaldehyde (DHMB);

(ii) 0.197 mole of vanillin.

350 cm³ of toluene and the quantity of amine given in the table below were added.

The mixture was heated to 100° C., under stirring and the pH was adjusted to 10.

This pH value was maintained throughout the period of the experiment by injecting a 30% by weight aqueous sodium hydroxide solution.

A methyl chloride pressure of 4 bars was established and this value was maintained throughout the period of the experiment.

After 4 hr or 5 hr (the time is given in the table below) of reaction, the final reaction mixture was cooled and treated as described in Example 1a.

The table below gives the CR of vanillin and of DHMB as well as the Y of 3,4-dimethoxybenzaldehyde (DMB), of trimethoxybenzaldehyde (TMBA) and of hydroxydimethoxybenzaldehydes [(HDMB) originating from the etherification of a single OH group of DHMB] respectively.

TABLE

| EXAMPLES | Amine and quantity | Time | CR of DHMB % | Y of TMBA % | Y of HDMB % | CR of vanillin % | Y of DMB % |
|---|---|---|---|---|---|---|---|
| Example 10 | triethanolamine 24 g (0.161 mole) | 5 hr | 97 | 80 | 20 | 88 | 96 |
| Example 11 | n-octylamine 22 g (0.170 mole) | 4 hr | 97 | 83 | 14 | 93 | 95 |
| Example 12 | N,N-dimethyl-benzylamine 23 g (0.170 mole) | 5 hr | 99 | 85 | 12 | 92 | 97 |
| Example 13 | triocylamine 57 g (0.161 mole) | 4 hr | 100 | 99 | 0 | 100 | 100 |
| Example 14 | tributylamine 36.5 g (0.197 mole) | 4 hr | 100 | 96 | 0 | 100 | 100 |
| Example 15 | N,N-dimethyl-aniline 21 g (0.173 mole) | 5 hr | 98 | 73 | 21 | 88 | 94 |
| Example 16 | triethylene-diamine 20 g (0.238 mole) | 4 hr | 97 | 75 | 20 | 86 | 100 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a 4,5-dialkoxy-3-methoxybenzaldehyde, comprising (a) hydrolyzing 5-bromo-4-hydroxy-3-methoxybenzaldehyde with an alkali metal hydroxide, and then (b) directly sequentially etherifying the 4,5-dihydroxy-3-methoxybenzaldehyde thus produced with a lower alkyl halide, in an aqueous medium and at a pH maintained at a value of from 6 to 12.

2. The process as defined by claim 1, comprising carrying out said hydrolysis (a) in water and in the presence of a catalytically effective amount of a copper catalyst.

3. The process as defined by claim 2, comprising carrying out said etherification (b) in the presence of a catalytically effective amount of an etherification catalyst.

4. The process as defined by claim 2, said copper catalyst comprising from 1 to 10 mole % of the amount of 5-bromo-4-hydroxy-3-methoxybenzaldehyde.

5. The process as defined by claim 4, said lower alkyl halide comprising a methyl or ethyl halide.

6. The process as defined by claim 5, said lower alkyl halide comprising methyl or ethyl chloride or bromide.

7. The process as defined by claim 5, comprising utilizing a stoichiometric excess of said lower alkyl halide.

8. The process as defined by claim 2, comprising carrying out the etherification reaction (b) in a two-phase reaction medium which comprises water and a water-immiscible organic solvent.

9. The process as defined by claim 8, said water-immiscible organic solvent comprising an aromatic hydrocarbon, aliphatic hydrocarbon, chlorinated aromatic hydrocarbon, or an aliphatic, aromatic or arylaliphatic ether.

10. The process as defined by claim 2, comprising carrying out the hydrolysis (a) at a temperature of from 50° C. to 250° C.

11. The process as defined by claim 2, comprising carrying out the etherification reaction (b) at a pH of from 9 to 11.

12. The process as defined by claim 2, comprising carrying out the etherification reaction (b) at a temperature of from 50° C. to 150° C.

13. The process as defined by claim 2, comprising carrying out the etherification reaction (b) at a pressure of from atmospheric pressure to 50 bars.

14. The process as defined by claim 3, comprising carrying out the etherification reaction (b) in the presence of a primary, secondary or tertiary amine catalyst, or a quaternary ammonium salt catalyst.

15. The process as defined by claim 14, said catalyst comprising an aliphatic, aromatic, arylaliphatic, alicyclic or heterocyclic primary or secondary amines; a tertiary amine; a cycloalkylalkylamine; a benzylalkylamine; a phenylalkylamine; a cyclic amine; or an alkyl, cycloalkyl or benzyl halide, hydroxide or sulfate of such amines.

16. The process as defined by claim 3, wherein the molar ratio between the etherification reaction catalyst and the 4,5-dihydroxy-3-methoxybenzaldehyde and any other hydroxybenzaldehydes present, ranges from 0 to 30%.

17. A process for the preparation of a 4,5-dialkoxy-3-methoxybenzaldehyde, comprising (a) hydrolyzing 5-bromo-4-hydroxy-3-methoxybenzaldehyde with an alkali metal hydroxide, and then (b) free from separating or isolating any reaction intermediate compounds including 4,5-dihydroxy-3-methoxybenzaldehyde, etherifying the 4,5-dihydroxy-3-methoxybenzaldehyde thus produced with a lower alkyl halide, in an aqueous medium and at a pH maintained at a value of from 6 to 12.

* * * * *